US006358476B1

(12) United States Patent
Innamorato et al.

(10) Patent No.: US 6,358,476 B1
(45) Date of Patent: Mar. 19, 2002

(54) MICROCOLLECTION TUBE ASSEMBLY

(76) Inventors: Sharon A. Innamorato, 37 W. Franklin Ave., Pequannock, NJ (US) 07440; Steven M. Rosen, 22 Blvd., Mountain Lakes, NJ (US) 07046; Volker Niermann, 196B Main St., Little Falls, NJ (US) 07042; Stewart E. Marsden, 20 Aynsley Ct., Montville, NJ (US) 07045

( * ) Notice: Subject to any disclaimer, the term of this patent is extended or adjusted under 35 U.S.C. 154(b) by 0 days.

(21) Appl. No.: 09/404,497

(22) Filed: Sep. 23, 1999

(51) Int. Cl.[7] .............................. B01L 3/14; B01L 9/06; B65D 35/00; C12M 1/24

(52) U.S. Cl. .................... 422/102; 422/104; 435/288.1; 604/403; 220/23.89

(58) Field of Search ................................ 422/102, 104; 435/288.1; 604/403; 220/23.89, 513

(56) References Cited

U.S. PATENT DOCUMENTS

| | | | | |
|---|---|---|---|---|
| 3,918,920 A | * 11/1975 | Barber | ........................ | 248/314 |
| 5,137,693 A | * 8/1992 | Mawhirt | ...................... | 422/104 |
| 5,456,887 A | 10/1995 | Calvo et al. | ................ | 422/104 |
| 5,458,854 A | 10/1995 | Burns | .......................... | 422/102 |

* cited by examiner

*Primary Examiner*—John Kim
(74) *Attorney, Agent, or Firm*—Richard E. Brown

(57) ABSTRACT

A blood collection assembly designed for one-time use includes a microcollection tube and an adapter for the tube which is sized to fit into the tube slot of an automated analytical instrument. The adapter includes structure which forms a tight and permanent interference fit with the micro-tube so that the tube, once inserted into the adapter, cannot be removed by hand, and the assembly, after sampling and analysis, must be discarded in one piece.

7 Claims, 7 Drawing Sheets

MICROCOLLECTION TUBE ASSEMBLY

BACKGROUND OF THE INVENTION

1. Field of the Invention

This invention relates to blood microcollection assemblies, and more particularly relates to a microcollection assembly which is compatible with analytical instrumentation.

2. Background

In modern medical practice, a variety of chemical and hematological diagnostic procedures are carried out on very small quantities of blood. In recent years, many collection assemblies have been disclosed for drawing, transporting and analyzing these small samples. In order to protect a phlebotomist or technician from contact with a contaminated blood sample, it has become conventional to draw these samples in equipment designed for single use followed by strict throw away procedures. Nevertheless, it does happen that attempts are made to reuse such equipment, either through operator error or misguided attempts to achieve economy.

In designing collection assemblies, an important factor to consider is compatibility of the blood sampling equipment with modern automated instrumentation. Thus, the small containers advantageously used are often not compatible with instruments designed generally for larger containers.

Adapters to render small sample collection tubes instrument-compatible have been disclosed. These adapters, however, are not designed for single use and instead provide means to separate the adapter from the collection tube for reuse after analysis. Reuse subjects the user to possible contact with a potentially dangerous blood sample.

There is a need in the art of blood collection for a device which would modify a microcollection tube to a size and shape which would enable its insertion directly into an automated blood analyzer, and at the same time have structure assuring one time throw-away use which cannot be defeated by a user wishing to reuse all or part of the assembly. It is toward fulfillment of this need that this invention is directed.

SUMMARY OF THE INVENTION

One aspect of the invention is an adapter for a blood microcollection container which renders the container compatible with automated analytical instruments. The adapter includes a sleeve dimensioned to fit into the slot of the instrument. A shelf which serves as a false bottom divides the sleeve into upper and lower segments which separate the interior volume of the sleeve into upper and lower regions. A tubular body in the upper region projects upwardly from the shelf and has structure thereon to form a permanent interference fit with a microcollection container inserted through an open end of the sleeve.

In an alternate embodiment of the adapter, the sleeve has longitudinal ribs on the inside surface of its upper segment which form an interference fit with the tube.

Another aspect of the invention is a blood microcollection assembly which includes the adapter, a microcollection container therein and a cap for the container.

Thus, the invention provides an instrument-compatible assembly for blood sampling in which the tube and adapter are permanently affixed by structure which prevents their being separated so that a user cannot defeat the one-time use only purpose of the assembly.

DETAILED DESCRIPTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. The scope of the invention will be measured by the appended claims and their equivalents.

The invention contemplates an adapter dimensioned to render any conventional blood microcollection container compatible with the container slot of an automated analysis instrument Such slots are generally 13 or 16 mm in external diameter and 75 or 100 mm long. Preferred microcontainers are Microtainer® Brand blood collection tubes sold by Becton Dickinson and Co. and the invention will henceforth be described for a microcollection tube. These preferred tubes and mating caps are fully described in U.S. Pat. No. 5,458,854 to Burns. Another aspect of the invention is a blood collection assembly in which a tube and mating cap are positioned in the adapter.

Figure 1:
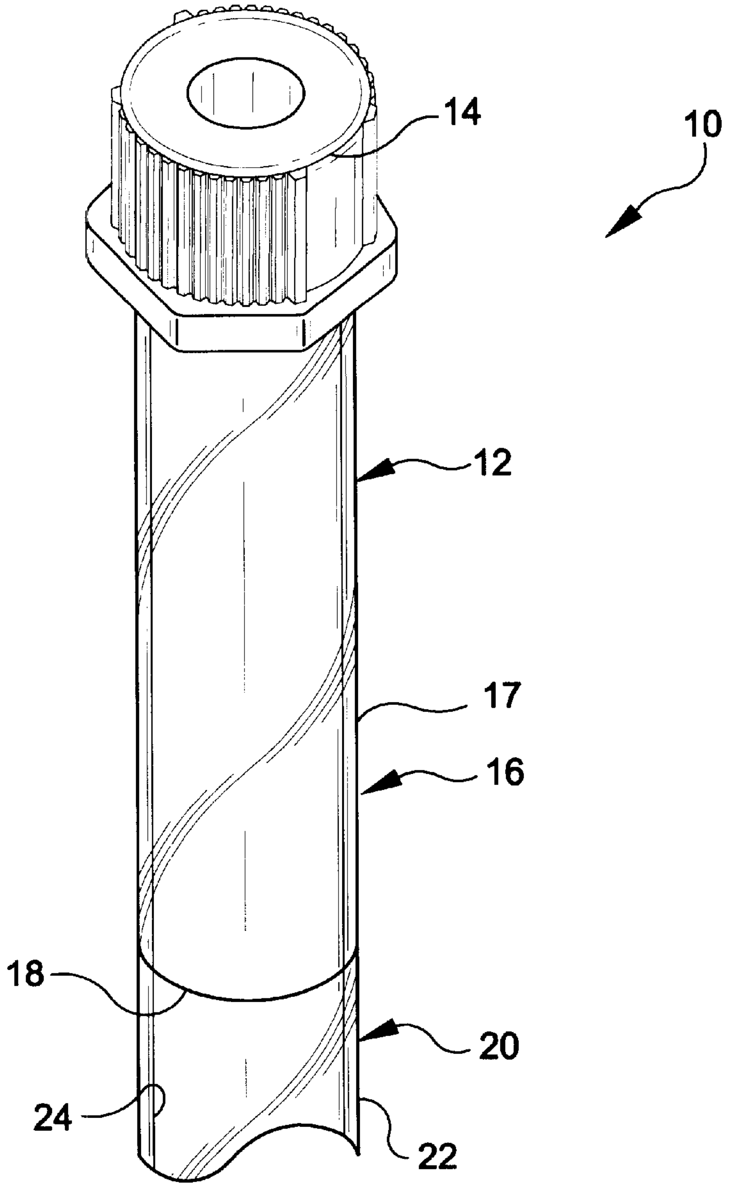
FIG. 1 is a perspective view of the tube and cap of the invention.

Adverting now to the drawings, FIG. 1 illustrates a preferred tube-cap unit 10 as disclosed in the aforementioned U.S. Pat. No. 5,458,854. Unit 10 includes a blood microcollection tube 12 having cap 14 covering an open top end thereof. Tube 12 has side wall portion 16 with outside wall surface 17 and bottom wall 18. Skirt 20 depends downwardly from sidewall 16 and is integral therewith. (In this disclosure the term integral means continuous, such as formed by injection molding). Skirt 20 has outside wall surface 22 and inside wall surface 24.

Figure 2:
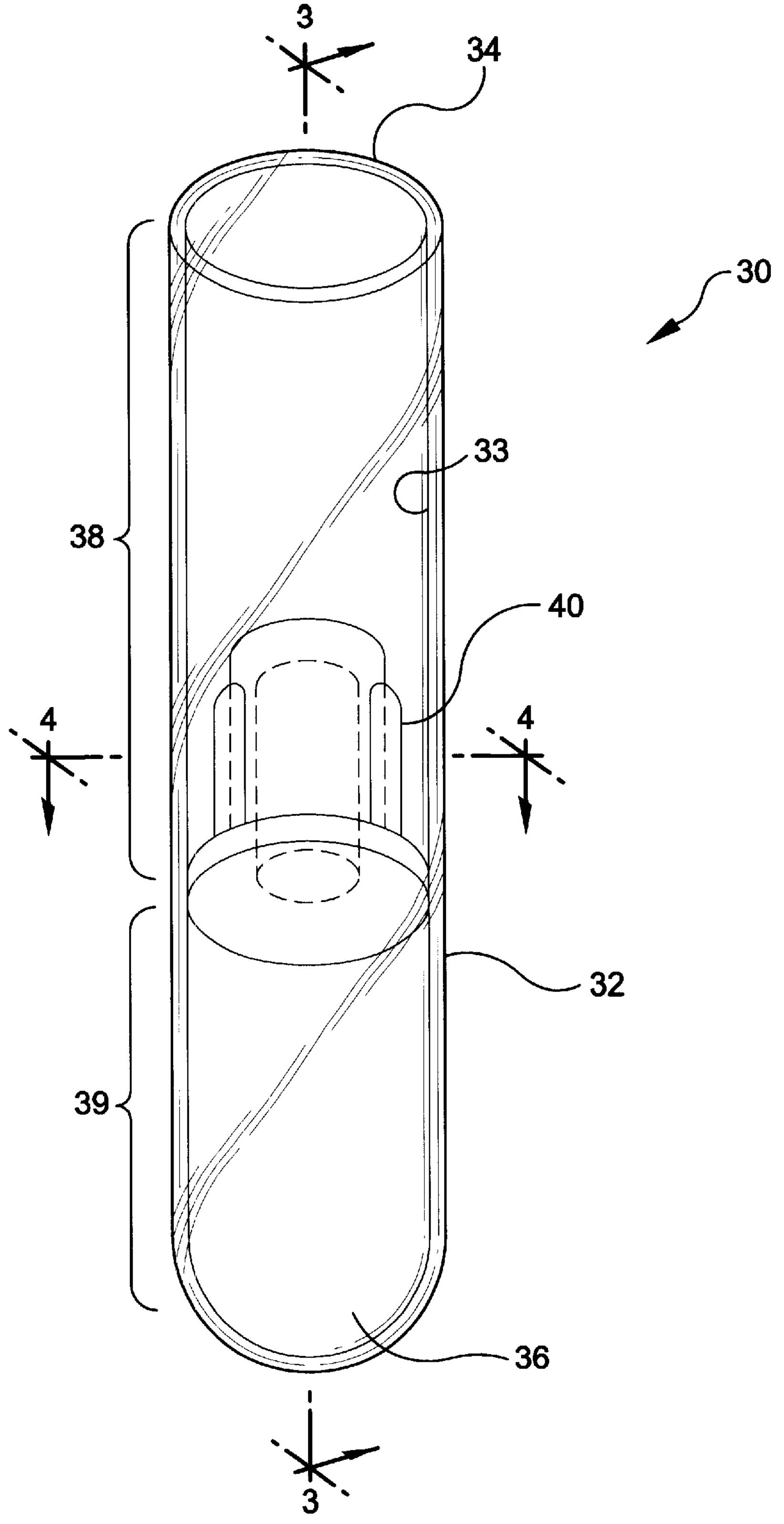
FIG. 2 is a perspective view of the adapter of the invention.
Figure 3:
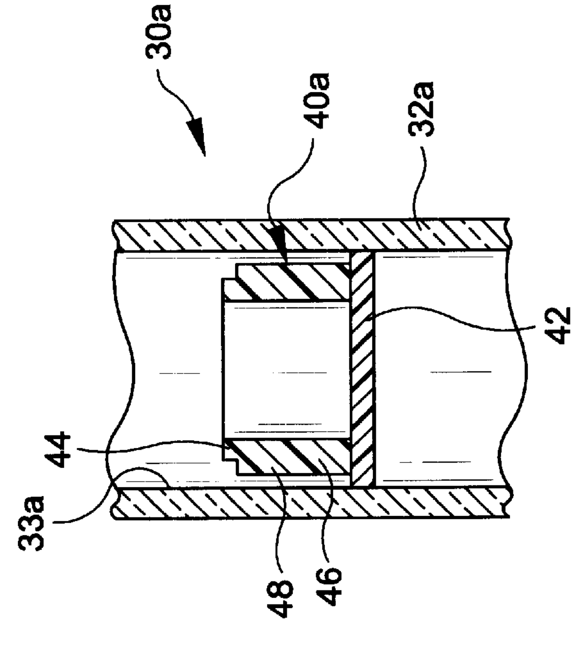

FIGS. 2 and 3 illustrate the adapter of the invention. In FIG. 2, adapter 30 is shown to include a sleeve 32 having inside wall surface 33 and an open top end 34. An integral bottom wall 36 is preferably curved as shown to form a better fit in a slot of an automated instrument. Sleeve 32 has upper segment 38 and lower segment 39. Lower segment 39 of sleeve 32 may preferably be textured (not shown in the drawing), as for example by conventional etching or frosting. The texture mimics an adapter slot filled to the top of the texture and causes the instrument sensor to move up and thereby read a tube in the upper segment 38. Adapter 30 includes structure 40, shown in phantom in FIG. 2 and in section in FIG. 3.

Figure 4:
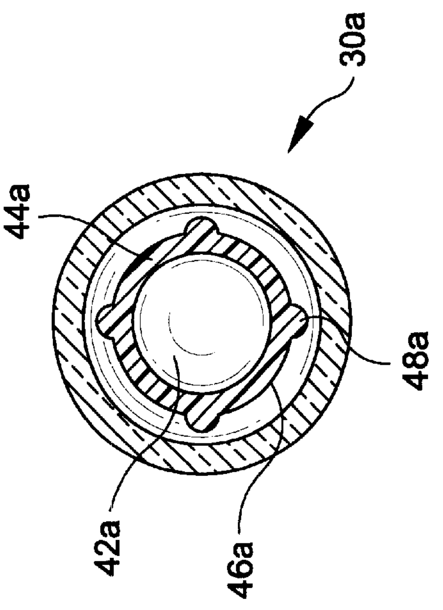
FIGS. 3 and 4 are vertical and horizontal sectional views respectively of the adapter of FIG. 2 taken along the lines 3—3 and 4—4 thereof.

In FIG. 3, details of structure 40 are illustrated. (In the drawings, elements which are the same or substantially the same in the various embodiments of the invention are given the same reference number followed by a lower case letter). A shelf 42, which serves as a false bottom for adapter 30*a*, positions a tube (not shown) to be immobilized in the adapter at the proper position for reading a bar code on the tube when the assembly of the invention is inserted in an automated analyzer. Shelf 42 may be either a disc or a rim. Tubular body 44 projects perpendicularly up from shelf 42 and has, on its outside wall surface 46, a plurality of rounded protuberances 48 integral with body 44. FIG. 4 is a sectional view of the adapter of FIG. 2 showing details of structure 40 as seen from the top.

Figure 5:
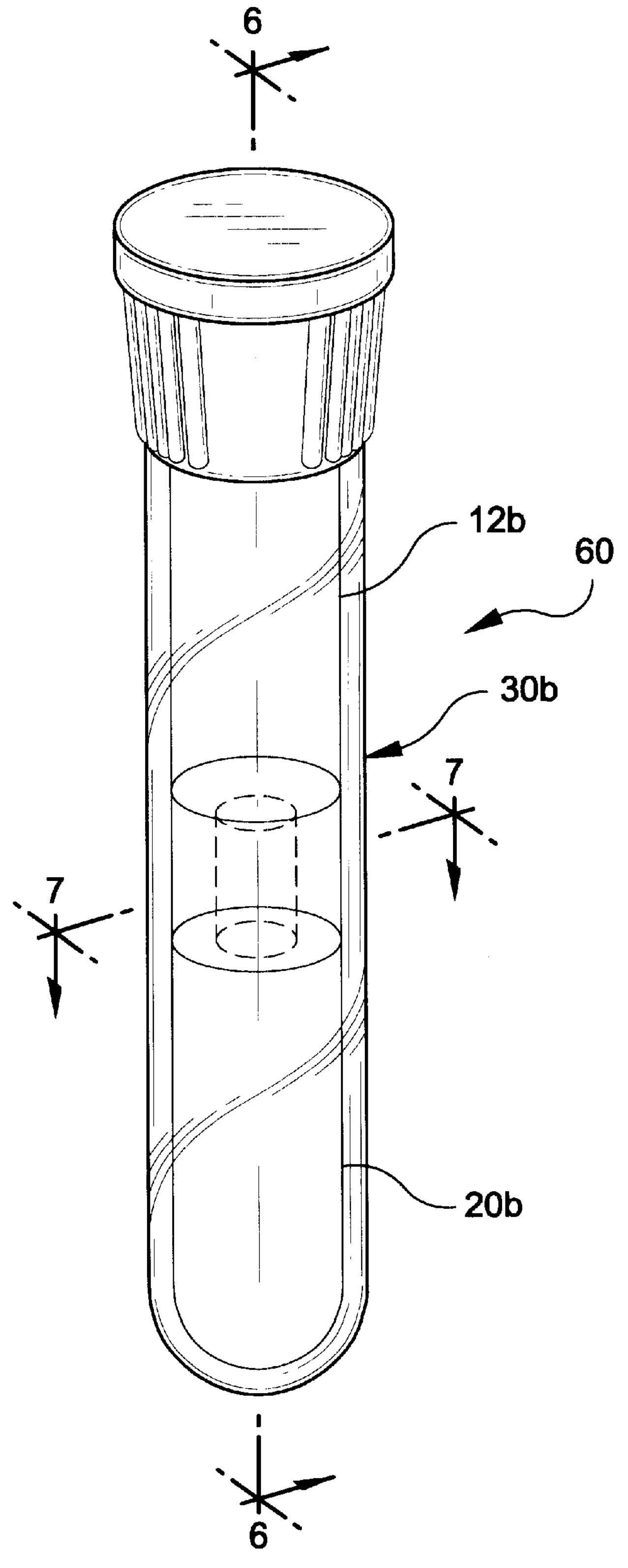
FIG. 5 is a perspective view of the assembly of the invention.
Figure 7:
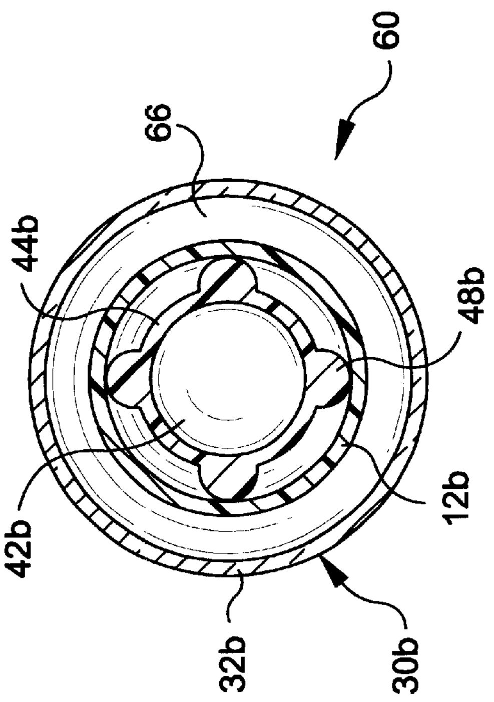
FIGS. 6 and 7 are vertical and horizontal sectional views respectively of the assembly, taken along the lines 6—6 and 7—7 of FIG. 5, with the tube in the adapter.
Figure 6:
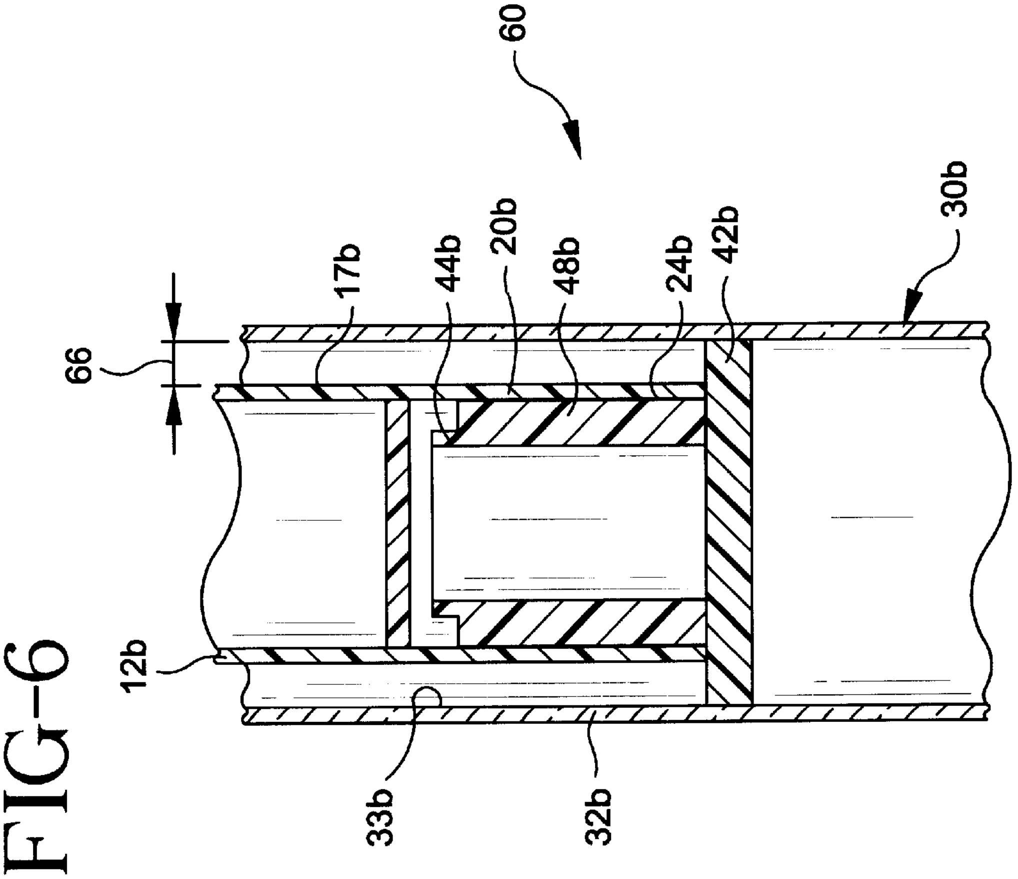

The tube-cap unit and the adapter may be combined in a blood collection assembly. As shown in FIGS. 5–7, assembly 60 includes adapter 30*b* having inside wall 33*b*, shelf 42*b* and tubular body 44*b* with integral protuberances 48*b*. Tube 12*b* having skirt 20*b* is permanently immobilized in adapter 30*b* by a tight interference fit between skirt inside wall 24*b* and protuberance 48*b*. It is seen that outside wall surface 17*b* of the tube is spaced at a distance 66 from inside wall surface 33*b* of adapter 30*b*. This space assures that any label, such as a patient information label previously applied to the tube, will not be scratched, crumpled, jammed or in any way be rendered illegible when the tube is immobilized in the adapter.

Figure 9:
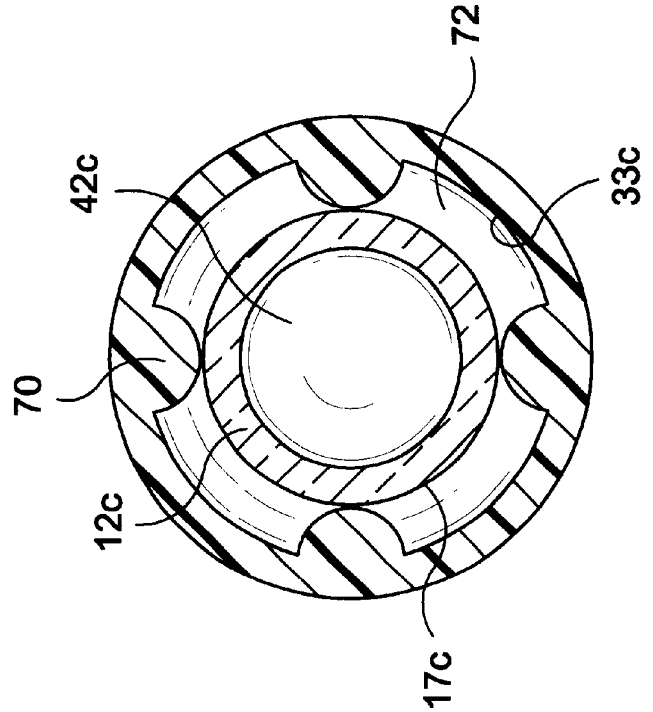
FIGS. 8 and 9 are sectional views of an alternative embodiment of the invention.
Figure 8:
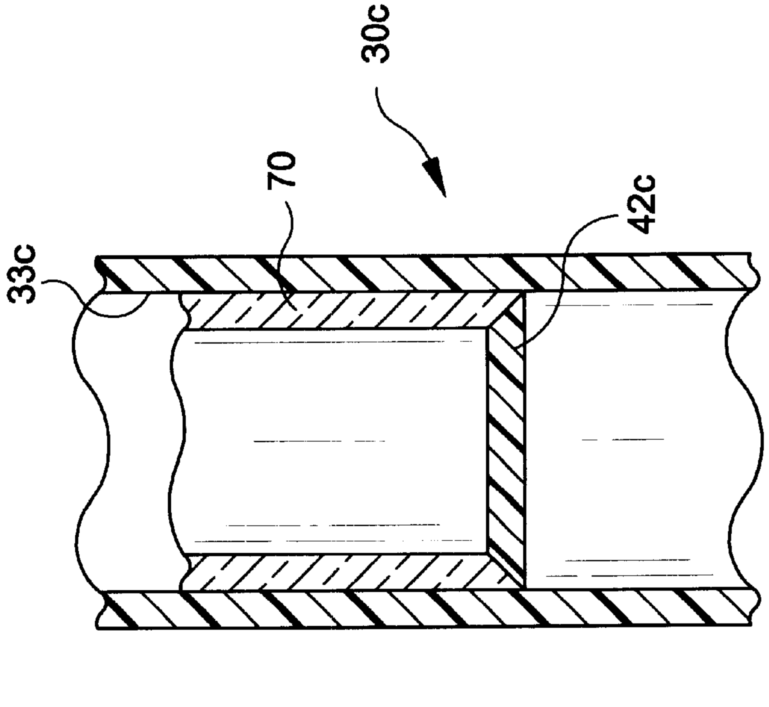

Another embodiment of the invention is illustrated in FIGS. 8 and 9. In this embodiment, inside wall surface 33*c* of adapter 30*c* has a longitudinal rib 70 integral therewith so that the interference fit which immobilizes the tube in the adapter occurs between the outside surface 17*c* of the tube and the rib. In this embodiment, the interference fit between the outer surface of the tube and the rib leaves space 72 (FIG. 9) so that, in this arrangement, a label on the outside of the tube will not be defaced when the tube is inserted into the adapter.

Figure 10:
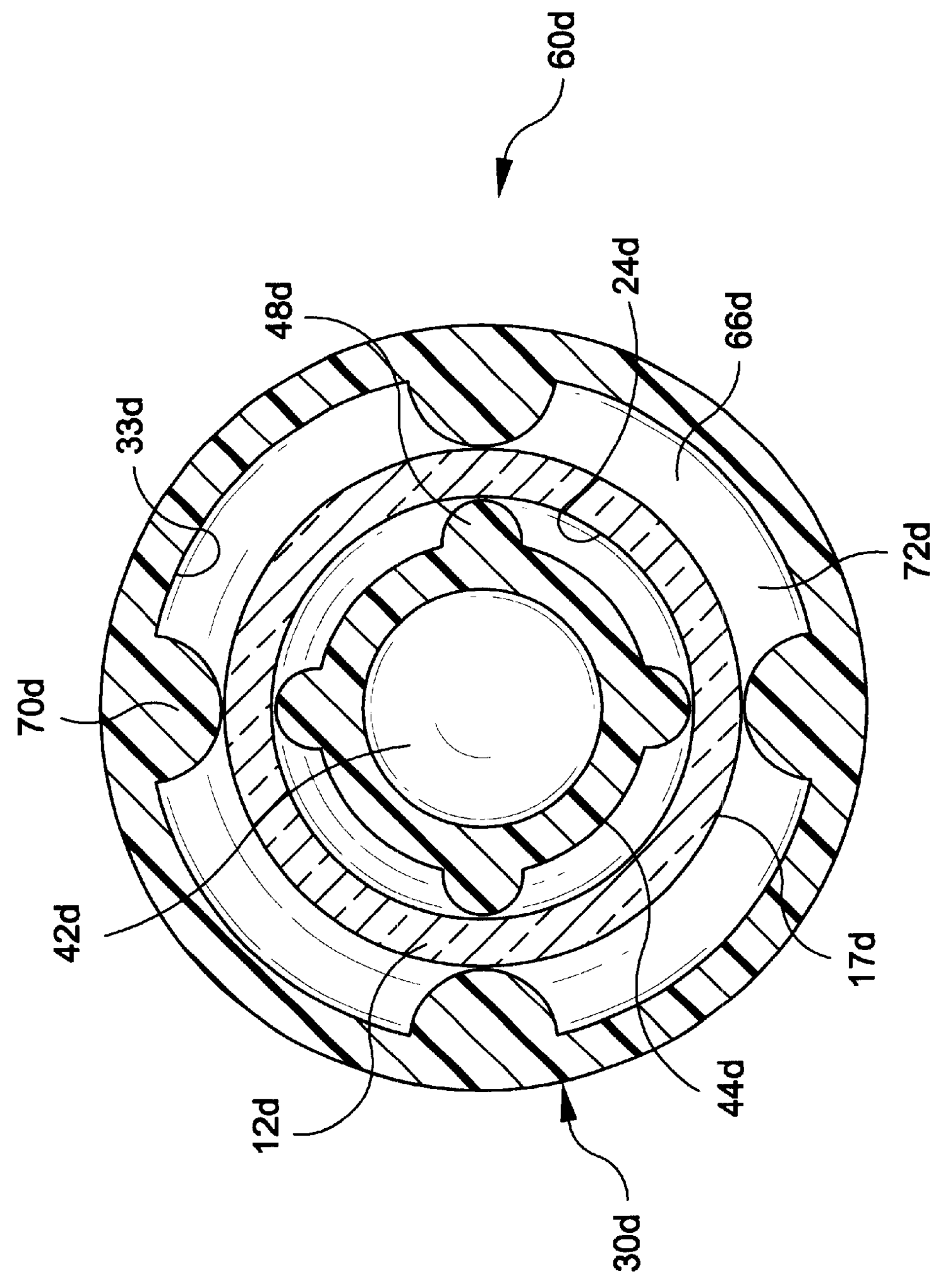
FIG. 10 is a horizontal sectional view of an embodiment of the invention combining the features of FIGS. 6 and 8.

Still another embodiment of the invention, illustrated in FIG. 10, combines the immobilization features of FIGS. 6 and 8. Inside wall surface 33*d* of the adapter 30*d* has longitudinal rib 70*d* integral therewith. Rib 70*d* forms an interference fit with the outside wall surface 17*d* of tube 12*d*, as in the embodiment of FIGS. 8 and 9. In addition, the inside wall surface 24*d* of the tube skirt forms an interference fit with protuberance 48*d* on tubular body 44*d*, as in the embodiment of FIGS. 5 to 7. The double interference fit thereby achieved between the adapter and both the inside and outside wall surfaces of the tube provides even greater assurance that the interlock between the tube and the adapter cannot be overcome by a user attempting to defeat its purpose.

The adapter of the invention may be of any plastic suitable for injection molding, such as polyethylene, polypropylene or polyvinyl chloride. The preferred adapter is clear plastic, preferably textured as described above, so that the bar code or any patient label on the tube can be read directly through the sleeve wall. The adapter may be of several molded parts affixed together into a single unitary device, or most preferably, may be injection molded into a single, integral device in which all components are continuous.

What is claimed is:

1. An adapter for a microcollection container comprising:

a) a sleeve having a bottom wall and a side wall, said side wall defining an open top end and an interior volume within said sleeve;

b) means integral with said side wall for dividing said sleeve into upper and lower segments defining upper and lower portions respectively of said interior volume;

c) a tubular body integral with and projecting perpendicularly upward from said means for dividing; and d) a plurality of rounded protuberances integral with the outside wall of said tubular body for forming an interference fit with the inside wall of a skirt of a microcollection container.

2. The adapter of claim 1 wherein said lower segment is textured.

3. The adapter of claim 1 further comprising a longitudinal rib on said side wall for forming an interference fit with an outside wall of a microcollection container.

4. An assembly for taking a blood sample comprising:

a) the adapter of claim 1;

b) a blood microcollection container immobilized in said upper portion; and c) a cap for said container.

5. The assembly of claim 4 wherein said assembly has an external diameter of 13 or 16 mm and a length of 75 or 100 mm.

6. The adapter of claim 1 wherein said means is a shelf, a disc or a rim.

7. An adapter for a microcollection container assembly comprising:

a) a sleeve having a bottom wall and a side wall defining an open top end and an interior volume within said sleeve;

b) a shelf perpendicular to and integral with said side wall, said shelf dividing said sleeve into an upper segment and a lower segment;

c) a tubular body integral with and projecting upwardly from said shelf;

d) a plurality of rounded protuberances integral with the outside wall of said tubular body for forming an interference fit with the inside wall of a skirt of a microcollection container; and e) a longitudinal rib on said side wall for forming an interference fit with an outside wall of a microcollection container.

* * * * *